US008333751B2

(12) United States Patent
Kobashi et al.

(10) Patent No.: US 8,333,751 B2
(45) Date of Patent: Dec. 18, 2012

(54) MEDICAL CONTAINER AND MEDICAL CONTAINER SET

(75) Inventors: Yoshihiko Kobashi, Hiroshima (JP); Naotsugu Ito, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 277 days.

(21) Appl. No.: 12/744,429

(22) PCT Filed: Nov. 19, 2008

(86) PCT No.: PCT/JP2008/070988

§ 371 (c)(1), (2), (4) Date: May 24, 2010

(87) PCT Pub. No.: WO2009/081671

PCT Pub. Date: Jul. 2, 2009

(65) Prior Publication Data

US 2010/0249728 A1 Sep. 30, 2010

(30) Foreign Application Priority Data

Dec. 25, 2007 (JP) ................................ 2007-332548

(51) Int. Cl.
*A61B 19/00* (2006.01)
*A61M 5/00* (2006.01)

(52) U.S. Cl. ....................................... 604/408; 604/262

(58) Field of Classification Search .................. 604/262, 604/403–410, 416

See application file for complete search history.

(56) References Cited

U.S. PATENT DOCUMENTS 5,125,919 A * 6/1992 Miller et al. ................. 604/408

FOREIGN PATENT DOCUMENTS

| | | | |
|---|---|---|---|
| JP | 2-9812 | | 3/1990 |
| JP | 2-9813 | | 3/1990 |
| JP | 2005-131221 | * | 5/2005 |
| JP | 2005-245960 | | 9/2005 |
| JP | 2006-087480 | | 4/2006 |
| JP | 2007-39121 | | 2/2007 |

* cited by examiner

*Primary Examiner* — Philip R Wiest

(74) *Attorney, Agent, or Firm* — Hamre, Schumann, Mueller & Larson, P.C.

(57) ABSTRACT

A medical container (1) includes a bag-like container body (10) made up of two flexible sheets (12*a*, 12*b*). At least one of a pair of long-side sealed areas (11La, 11Lb) formed by the two sheets being bonded together is provided with a sealed protruding portion (20*a*, 21*a*, 20*b*, 21*b*) protruding toward the other long-side sealed area such that the spacing between the pair of long-side sealed areas is locally narrowed. A crease (30*a*, 31*a*, 30*b*, 31*b*) passing through the sealed protruding portion is formed in the sheets when a liquid substance has been injected into the container body in a volume greater than or equal to 10% of a defined volume of the container body and the medical container is hung. Accordingly, it is possible to know the exact amount of a liquid substance in the container by using a scale provided on the sheets constituting the container even if a crease is formed in the sheets due to the liquid substance being in the container.

6 Claims, 4 Drawing Sheets

MEDICAL CONTAINER AND MEDICAL CONTAINER SET

TECHNICAL FIELD

The present invention relates to a medical container for storing a liquid substance that is administered to a patient when providing enteral nutrition, parenteral nutrition, and the like. Furthermore, the invention relates to a medical container set including the medical container.

BACKGROUND ART

Enteral nutrition and parenteral nutrition are known as methods for administering nutrition and medications to patients by routes other than by the mouth. With enteral nutrition, a liquid substance such as a nutrient, liquid food, or a medication is administered via a tube passed through the nasal cavity to the stomach or duodenum of the patient. With parenteral nutrition, on the other hand, a liquid substance (generally called an "infusion") containing a nutrient component such as glucose or a medication component is administered via an infusion line inserted into a vein of the patient.

When enteral nutrition or parenteral nutrition is provided, in general, a liquid substance prepared in a workroom is filled into a medical container, the container is then carried to the hospital room where the patient is, and the liquid substance is administered to the patient.

As a medical container used when providing enthral nutrition and parenteral nutrition, a medical container is known that is produced by forming two substantially rectangular flexible sheets into a bag by heat-sealing the sheets at their periphery, and attaching a port for introducing/discharging a liquid substance to/from the container to one end edge of the bag (e.g., see Patent documents 1 and 2). In order to check the amount of the liquid substance in the container when injecting the liquid substance into the container or when administering the liquid substance in the container to the patient, the sheets constituting the container are provided with a scale. The amount of the liquid substance in the container can be known, for example, by comparing the liquid level of the liquid substance in the container with the scale provided on the sheet in a state in which the container is hung.

Patent document 1: JP H2-009812Y2

Patent document 2: JP H2-009813Y2

DISCLOSURE OF INVENTION

Problem to be Solved by the Invention

Since a conventional container is produced by sealing two sheets at the periphery thereof so as to form a bag as described above, the container is flat when it is empty, but bulges into a substantially columnar shape when a liquid substance is injected into the container. The sheets themselves hardly stretch even when the liquid substance is injected into the container, so that a crease is formed in the sheets when the container bulges as a result of injecting the liquid substance. However, the position where the crease is formed is not constant; for example, the position varies depending on the amount of liquid substance injected, or varies each time a liquid substance is injected even if the amount of the liquid substance is the same. If the position of the crease formed in the container when a liquid substance is injected is not constant, then it is not possible to know the exact amount of the liquid substance in the container by using the scale provided on the sheet.

The present invention solves the above-described conventional problem, and it is an object of the invention to provide a medical container and a medical container set with which it is possible to know the exact amount of a liquid substance in the container by using a scale provided on sheets that constitute the container, even if a crease is formed in the sheets due to the liquid substance being in the container.

Means for Solving Problem

A medical container of the present invention includes a bag-like container body made up of two flexible sheets. The container body has a pair of long-side sealed areas formed by the two sheets being bonded together along two opposing sides that are substantially parallel to a major axis direction of the container body. At least one of the pair of long-side sealed areas is provided with a sealed protruding portion protruding toward the other long-side sealed area such that the spacing between the pair of long-side sealed areas is locally narrowed. A crease passing through the sealed protruding portion is formed in the sheets when a liquid substance has been injected into the container body in a volume greater than or equal to 10% of a defined volume of the container body and the medical container is hung such that the major axis direction is parallel to the direction of gravity.

A medical container set of the present invention includes the above-described medical container of the present invention and an enteral giving set including a flexible tube for removing a liquid substance stored in the container body.

Effects of the Invention

According to the present invention, a crease passing through the sealed protruding portion is formed in the sheets when a liquid substance is injected into the container body. Accordingly, the position of the crease is constant, so it is possible to know the exact amount of the liquid substance in the container body by using the scale provided on the sheet.

DESCRIPTION OF THE INVENTION

Figure 1:
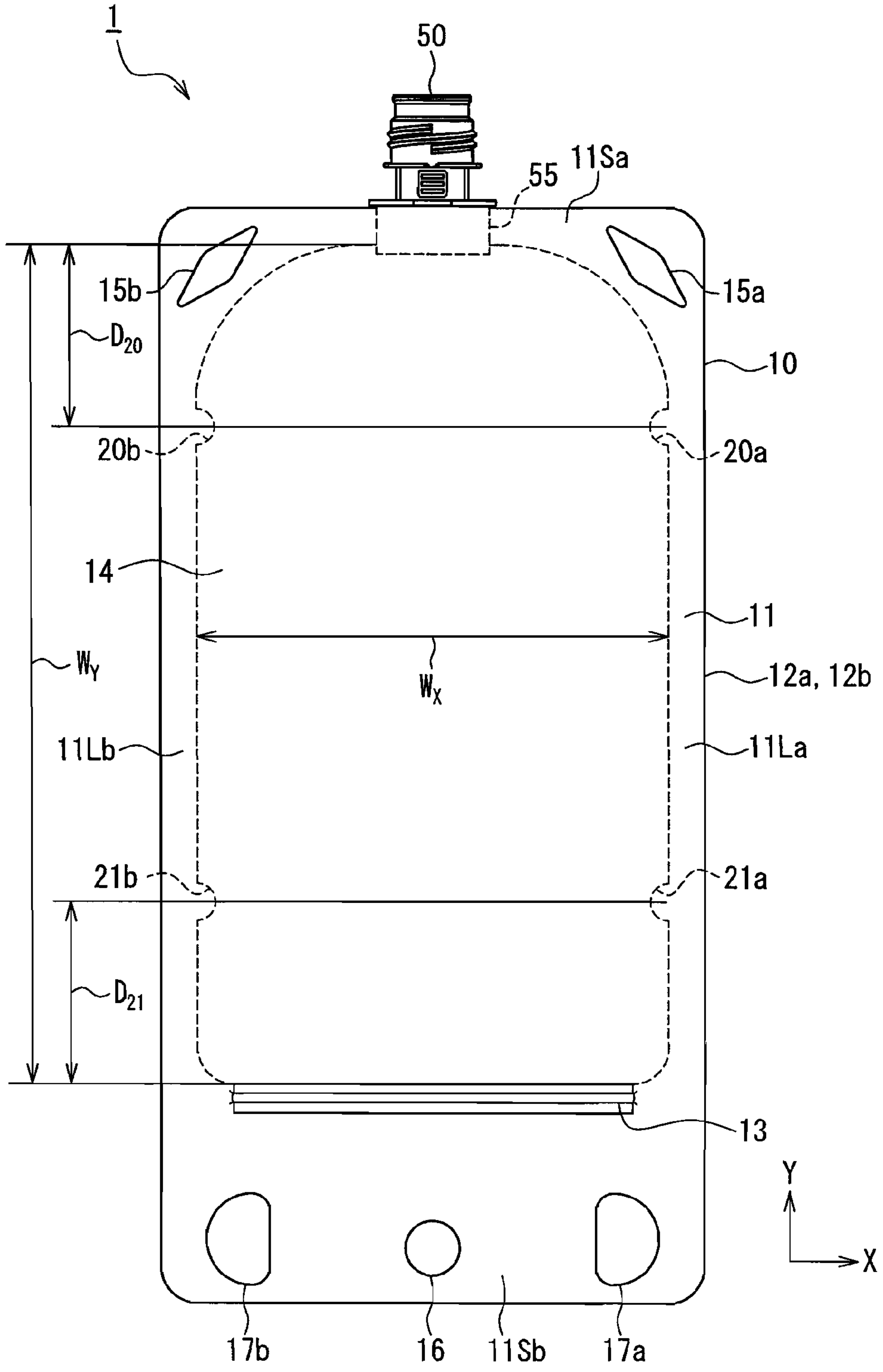
FIG. 1 is a front view showing a schematic configuration of an empty medical container according to one embodiment of the present invention.

According to the present invention, a crease passing through a sealed protruding portion is formed in sheets that constitute a container body when a liquid substance has been injected into the container body in a volume greater than or equal to 10% of a defined volume of the container body and the medical container is hung such that the major axis direction of the container body is parallel to the direction of gravity.

A "defined volume of the container body" refers generally to the maximum range indicated by the scale provided on the medical container.

The phrase "a crease passing through a sealed protruding portion is formed when a liquid substance has been injected into the container body in a volume greater than or equal to 10% of a defined volume of the container body and the medical container is hung" means that a crease passing through the sealed protruding portion is formed when the amount of the liquid substance injected takes a value greater than or equal to 10% of a defined volume of the container body. Accordingly, for example, in the case where the amount of the liquid substance injected into the container body is gradually increased from zero, the above-described condition is satisfied if a crease passing through the sealed protruding portion is formed for the first time when the amount of the liquid substance injected has reached 30% of a defined volume of the container body.

The reason that the state in which a liquid substance has been injected into the container body in a volume that is "greater than or equal to 10%" of a defined volume of the container body is used as a reference is because a crease may be formed in the sheets even if the liquid substance is injected into the container body in a volume less than a defined volume of the container body, and it may be necessary to accurately measure the amount of the liquid substance in the container body even in such a case.

The liquid substance that actually will be injected into the container body may be used as the "liquid substance" for determining whether or not a crease passing through the sealed protruding portion is formed. However, water may be used as an alternative, since the position where the crease is formed does not greatly vary according to the type of the liquid substance injected into the container body.

"To hang the medical container" means to suspend the medical container using gravity, while holding the upper end, relative to the direction of gravity, of the medical container. When the medical container is provided with a hanging mechanism (e.g., a hole, a protrusion, or the like), it is preferable to hang the medical container by using this mechanism. The reason is that this is similar to the state in which the medical container is actually used.

When "the medical container is hung such that the major axis direction of the container body is parallel to the direction of gravity", it is optional to hang the medical container with either end, in the major axis direction, of the container body at the top. As long as a crease passing through the sealed protruding portion is formed when the medical container is hung with one of the ends at the top, the position of the crease will be constant in such a hung state; accordingly, it is possible to measure the amount of the liquid substance in the container body accurately.

When a plurality of sealed protruding portions are formed, it is sufficient that a crease passing through at least one of the plurality of sealed protruding portions is formed. Additional creases that do not pass through the sealed protruding portion may be formed, but it is preferable that no such creases are formed.

In the above-described medical container of the present invention, it is preferable that the sealed protruding portion is formed in both of the pair of long-side sealed areas. Ordinarily, when a liquid substance is present in the container body, creases are formed such that they respectively pass through the pair of long-side sealed areas. Accordingly, the positions of the creases respectively passing through the pair of long-side sealed areas are constant if the sealed protruding portion is formed in both of the pair of the long-side sealed areas, whereby the amount of the liquid substance in the container body can be measured more accurately by using the scale provided on the sheet.

In this case, it is preferable that the positions, in the major axis direction, of the sealed protruding portions formed in both of the pair of long-side sealed areas coincide. This facilitates formation of symmetrical creases respectively passing through the sealed protruding portions that are formed respectively in the pair of long-side sealed areas, so that the amount of the liquid substance in the container body can be even more accurately measured by using the scale provided on the sheet.

Preferably, the sealed protruding portion is disposed on both sides across a central position, in the major axis direction, of an effective area of the container body capable of storing a liquid substance. This enables more accurate measurement of the amount of the liquid substance in the container body by using the scale provided on the sheet, regardless of the end in the major axis direction from which the container is hung.

Preferably, the sealed protruding portion has a substantially semicircular shape. This can mitigate concentration of stress on a portion of the sheets in the vicinity of the sealed protruding portion when the crease passing through the sealed protruding portion is formed, thus preventing tearing or the like of the sheet.

Preferably, the sealed protruding portion is located at a distance of ¼ to ½, inclusive, of the spacing between the pair of long-side sealed areas in the major axis direction from one end, in the major axis direction, of an effective area of the container body capable of storing a liquid substance. This increases the possibility that the crease formed in the sheet will pass through the sealed protruding portion when the container body in which a liquid substance is injected is hung such that its major axis direction is parallel to the direction of gravity. Moreover, when the spacing between the pair of long-side sealed areas is taken as $W_X$, it is preferable that the sealed protruding portion is located at a distance of $0.3 \times W_X$ or greater and $0.45 \times W_X$ or less from one end of the effective area of the container body in the major axis direction.

Hereinafter, a further detailed description of the present invention will be given while indicating a specific embodiment. However, it should be appreciated that the present invention is not limited to the embodiment shown below.

FIG. 1 is a front view showing a schematic configuration of a medical container (hereinafter, simply referred to as a "container") 1 in which a liquid substance has not been injected, according to one embodiment of the present invention. The container 1 of this embodiment includes a container body 10 and a port 50 for injecting a liquid substance into the container body 10 or removing a liquid substance stored in the container body 10.

The container body 10 is a bag-like article (what is called a "pouch") produced by bringing two soft, flexible, substantially rectangular sheets 12*a* and 12*b* of the same dimensions together, and bonding them at a sealed area 11 located at their periphery. As shown in FIG. 1, the major axis direction of the container body 10 (i.e., the long-side direction of the sheets 12*a* and 12*b*) is taken as the Y-axis, and the minor axis direction (i.e., the short-side direction of the sheets 12*a* and 12*b*) is taken as the X-axis. The portions of the sealed area 11 that extend along two opposing sides of the container body 10 that are parallel to the Y-axis direction are called "long-side sealed areas 11La and 11Lb", and the portions of the sealed area 11 that extend along two opposing sides of the container body 10 that are parallel to the X-axis direction are called "short-side sealed areas 11Sa and 11Sb". Of the container body 10, the area that is surrounded by the sealed area 11 and that can store a liquid substance is called an "effective area 14". The dimension of the effective area 14 in the X-axis direction (the spacing between the long-side sealed areas 11La and 11Lb along the X-axis direction; however, sealed protruding portions 20*a*, 20*b*, 21*a*, and 21*b* described below are excluded) is $W_X$, and the dimension of the effective area 14 in the Y-axis direction (the spacing between the short-side sealed areas 11Sa and 11Sb along the Y-axis direction) is $W_Y$.

The port 50 is attached to the short-side sealed area 11Sa of the container body 10, and provides communication between the interior and the exterior of the container body 10. Numeral 13 denotes a linear fastener that is provided along the short-side sealed area 11Sb and that can be repeatedly opened and closed, and an opening communicating with the interior of the container body 10 is formed when the linear fastener 13 is opened. Openings (through-holes) 15*a* and 15*b* for holding a tube 81 (see FIG. 4) constituting an enteral giving set 80 described below by inserting the tube 81 in a curved manner are respectively provided at a pair of corner portions where the short-side sealed area 11Sa intersects with the long-side sealed areas 11La and 11Lb, and an opening (through-hole) 16 for hanging the container 1 and openings (through-holes) 17*a* and 17*b* for holding the container 1 with the linear fastener 13 being held open by inserting two fingers are formed in the short-side sealed area 11Sb.

Sealed protruding portions 20*a* and 21*a* protruding toward the long-side sealed area 11Lb are formed in the long-side sealed area 11La, and sealed protruding portions 20*b* and 21*b* protruding toward the long-side sealed area 11La are formed in the long-side sealed area 11Lb. The end edge of each of the sealed protruding portions 20*a*, 21*a*, 20*b*, and 21*b* (the boundary between each of the sealed protruding portions and the effective area 14) has a substantially semicircular shape.

In the Y-axis direction, the sealed protruding portions 20*a* and 20*b* are provided in the same position, and the sealed protruding portions 21*a* and 21*b* are provided in the same position. With respect to the central position of the effective area 14 in the Y-axis direction, the sealed protruding portions 20*a* and 20*b* are disposed on the short-side sealed area 11Sa side, and the sealed protruding portions 21*a* and 21*b* are disposed on the short-side sealed area 11Sb side. When the distance in the Y-axis direction from the central position, in the Y-axis direction, of each of the sealed protruding portions 20*a* and 20*b* to the short-side sealed area 11Sa is taken as $D_{20}$, the distance in the Y-axis direction from the central position, in the Y-axis direction, of each of the sealed protruding portions 21*a* and 21*b* to the short-side sealed area 11Sb is taken as $D_{21}$, it is possible, as an example, for $D_{20}$ to be 60 mm, and $D_{21}$ to be 50 mm. In this example, $W_X$ is 130 mm, and $W_Y$ is 250 mm.

There is no particular limitation with respect to the material of the sheets 12*a* and 12*b* constituting the container body 10; ordinarily, a composite sheet having two or more layers is used. For example, it is possible to use a composite sheet including an inner layer and an outer layer that are formed of the same material or different materials selected from plastic materials such as polyethylene terephthalate, nylon, polypropylene, or polyethylene. A thin film of aluminum oxide, silica, or the like may be formed as a barrier layer onto the composite sheet. When two sheets are sealed by a commonly used heat-sealing method, each of the sheets is provided with a heat-sealing layer on the surface facing the other sheet. In order to allow the amount and the like of the liquid substance in the container body 10 to be checked, it is preferable that at least one of the two sheets 12*a* and 12*b* be transparent or semitransparent. In addition, a scale for determining the amount of the liquid substance in the container body 10 in a state in which the container 1 is hung may be provided on at least one of the two sheets 12*a* and 12*b*, for example, by printing.

Figure 2:
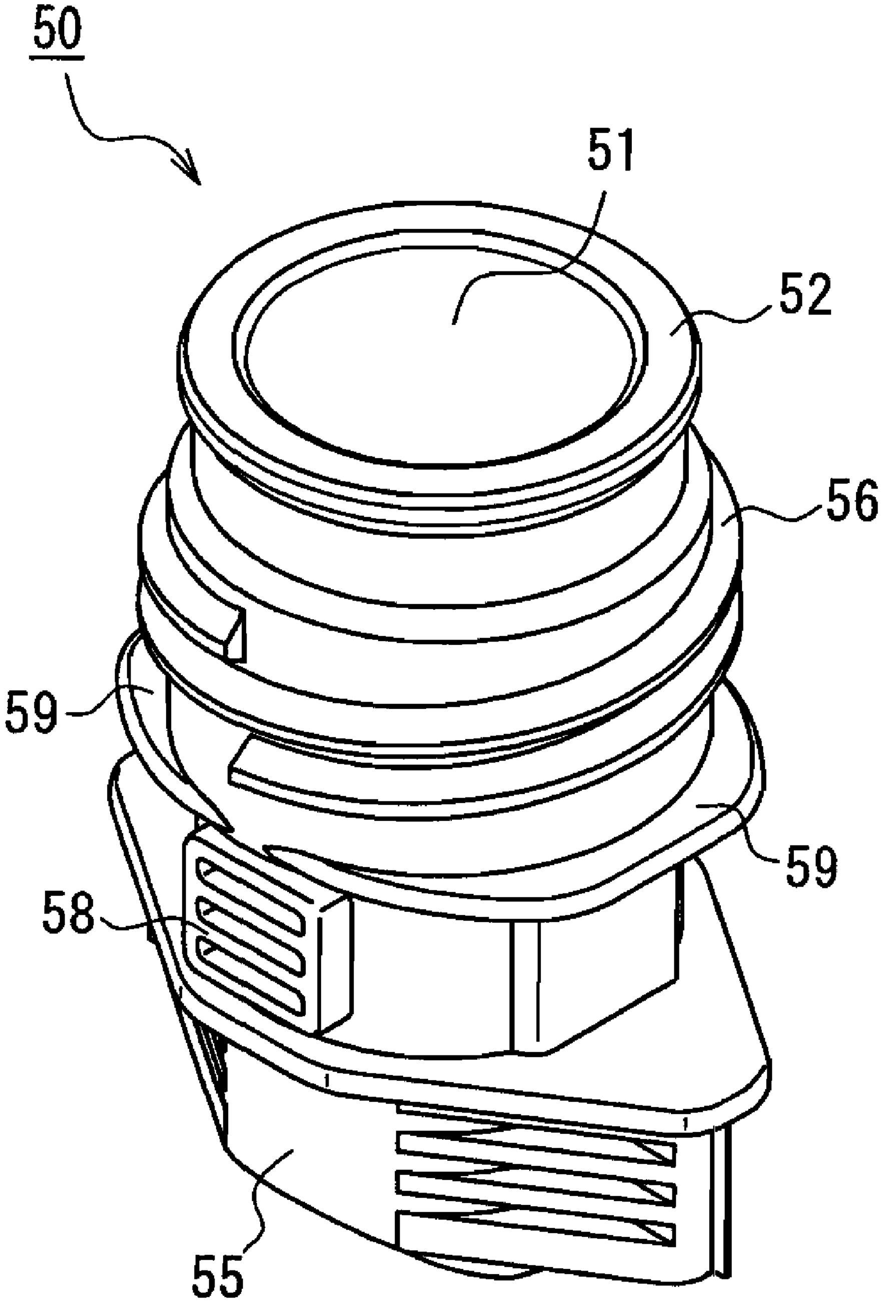
FIG. 2 is a perspective view showing a schematic configuration of a port used for a medical container according to one embodiment of the present invention.

FIG. 2 is a perspective view of the port 50. The port 50 includes a cylindrical tubular portion 52 in which a liquid passage hole 51 for passage of a liquid substance is formed, a sealing portion 55 provided on the outer circumferential surface of the tubular portion 52 at one end or in the vicinity thereof, and a cap mounting portion 56 formed on the outer circumferential surface of the tubular portion 52 at the other end. A holding portion 58 and flange portions 59 are formed on the outer circumferential surface of the tubular portion 52 between the sealing portion 55 and the cap mounting portion 56. The flange portions 59 are made up of flat plates protruding in directions orthogonal to the central axis of the tubular portion 52.

The sealing portion 55 has the shape of a quadrangular prism whose bottom surface is substantially rhombic. By sealing (e.g., heat-sealing or ultrasonically sealing) the peripheral edges of the two sheets 12*a* and 12*b*, which constitute the container body 10, with the sealing portion 55 of the port 50 being sandwiched between the peripheral edges of the two sheets, it is possible to integrate the port 50 and the container body 10 into one piece through bonding, simultaneously with formation of the sealed area 11 (see FIG. 1).

The cap mounting portion 56 is constituted by an external thread for mating with an internal thread formed on a cap to which one end of an enteral giving set, details of which will be described later, will be connected. However, the cap mounting portion 56 is not limited to this, and may be configured in any suitable shape that enables the cap to be mounted by engaging with the cap.

The port 50 is made of, for example, a relatively hard material compared to the sheets 12*a* and 12*b* constituting the container body 10, such as polyethylene, polypropylene, polyvinyl chloride, polyethylene terephthalate, an ethylene-vinyl acetate copolymer, a thermoplastic elastomer, or polyacetal, and can be formed integrally, for example, by injection molding.

A method for using the container 1 of this embodiment that is configured as described above and a function of the container will be described below.

The container 1 is suspended with the port 50 at the top, for example, by holding the holding portion 58 of the port 50 with two fingers, or allowing the flange portions 59 to be held by inserting a portion of the port 50 that is located between the sealing portion 55 and the cap mounting portion 56 into a substantially U-shaped jig. Then, a liquid substance used for enteral nutrition, parenteral nutrition, or the like is injected into container body 10 through the liquid passage hole 51 of the port 50.

Figure 3:
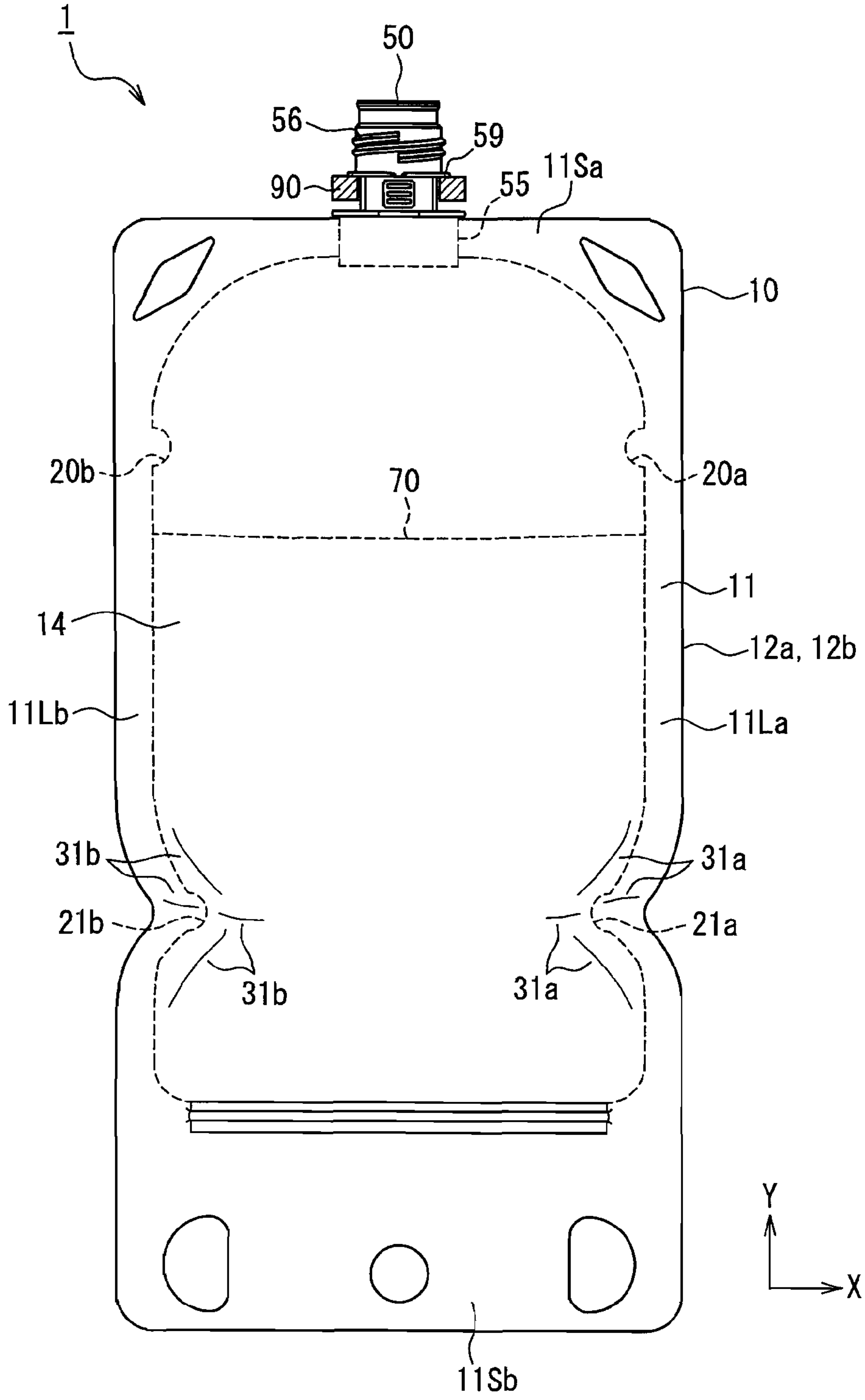
FIG. 3 is a front view showing a state in which a medical container according to one embodiment of the present invention, in to which a liquid substance has been injected, is suspended with the port at the top.

FIG. 3 is a front view showing a state in which a liquid substance has been injected into the container 1 that is hung by allowing the flange portions 59 of the port 50 to be held by a substantially U-shaped jig 90. By using the port 50 to hang the container 1, the port 50 is allowed to face upward with the major axis direction (Y-axis direction) of the container body 10 being substantially parallel to the direction of gravity. In FIG. 3, numeral 70 denotes the liquid level of the liquid substance. As shown in FIG. 3, creases 31*a* and 31*b* passing through the sealed protruding portions 21*a* and 21*b* are formed in the sheets 12*a* and 12*b* constituting the container body 10.

Before the liquid substance is injected, the effective area 14 of the container body 10 is flat with the sheets 12*a* and 12*b* being in close contact with each other, except for an area of the port 50 that is in the vicinity of the sealing portion 55. As the liquid substance is being injected, the liquid level 70 of the liquid substance rises and the spacing between the sheets 12*a* and 12*b* gradually expands in the effective area 14, as a result of which the effective area 14 bulges such that the shape of its cross section orthogonal to the Y-axis approaches a substantially circular shape. Since the liquid substance accumulates in the lower part of the effective area 14, the spacing between the sheets 12*a* and 12*b* is larger in the lower part of the effective area 14 than in the upper part thereof. On the other hand, the peripheries of the sheets 12*a* and 12*b* are in close contact due to the presence of the sealed area 11. Accordingly, the creases 31*a* and 31*b* passing through the lower sealed protruding portions 21*a* and 21*b* are formed in the sheets 12*a* and 12*b* as shown in FIG. 3. The depth of the creases 31*a* and 31*b* (the bending angle of the sheets 12*a* and 12*b*) increases with an increase in the amount of the liquid substance injected, but the creases 31*a* and 31*b* always pass through the sealed protruding portions 21*a* and 21*b*.

Figure 4:
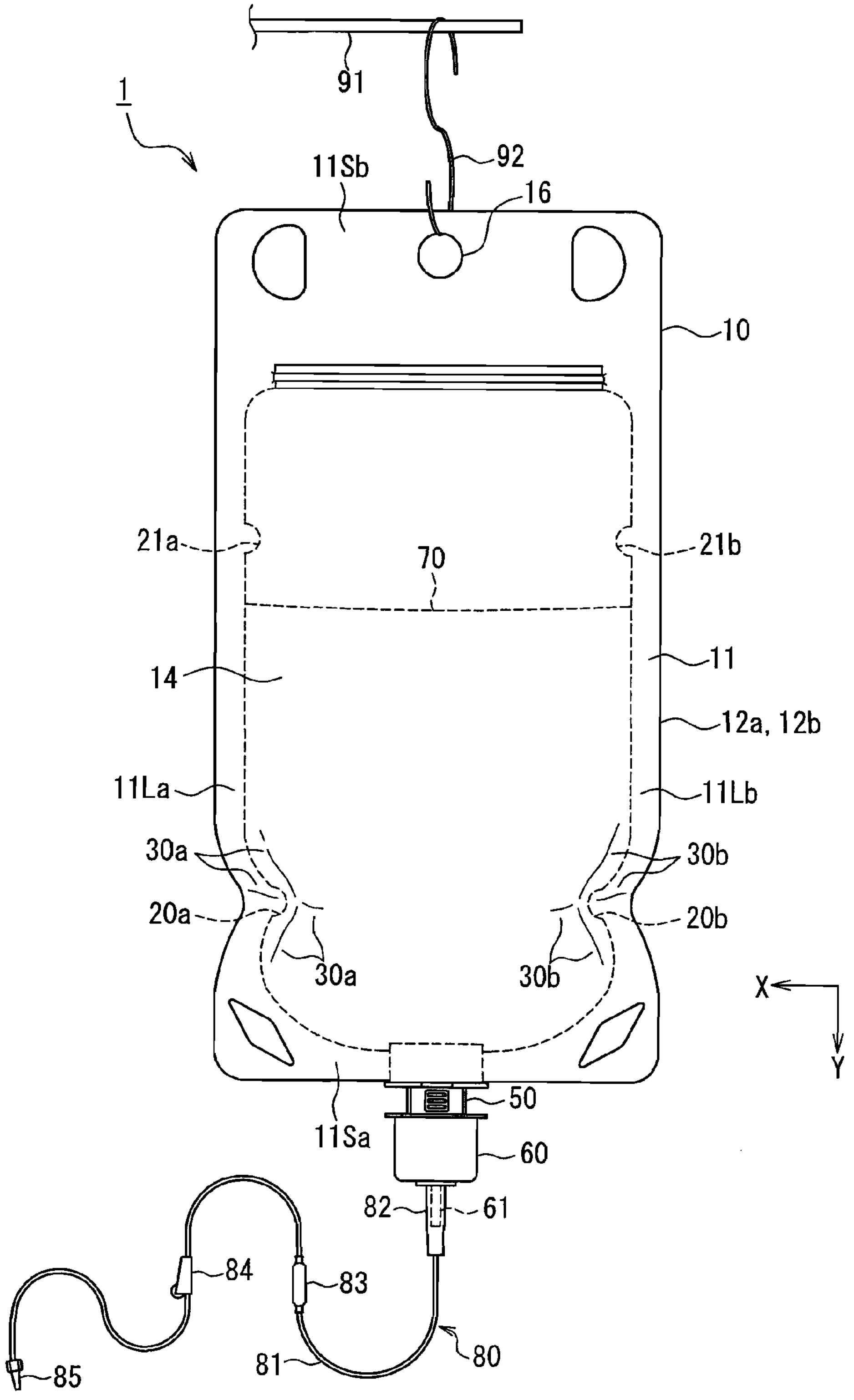
FIG. 4 is a front view showing a state in which a medical container according to one embodiment of the present invention, in to which a liquid substance has been injected, is suspended with the port at the bottom.

After a specific amount of the liquid substance is injected into the container 1, a cap is attached to the cap mounting portion 56 at the tip of the port 50, and an enteral giving set further is connected to the cap. Then, the container 1 is hung with the port 50 at the bottom. FIG. 4 shows a container 1 that is hung by inserting, through an opening 16 formed in the short-side sealed area 11Sb of the container body 10, an s-hook 92 that is hung on an irrigator stand 91. By using the opening 16 to hang the container 1, the port 50 is allowed to face downward with the major axis direction (Y-axis direction) of the container body 10 being substantially parallel to the direction of gravity. In FIG. 4, numeral 60 denotes a cap attached to the cap mounting portion 56 at the tip of the port 50. An internal thread (not shown) for mating with the external thread of the cap mounting portion 56 of the port 50 is formed on the cap 60. Numeral 80 denotes an enteral giving set that includes a flexible tube 81. The enteral giving set 80 shown in FIG. 4 is provided with a rubber tube 82 for fitting over a cylinder 61 provided in the cap 60 at one end of the tube 81, a drip chamber 83 and a clamp 84 for flow adjustment in the middle of the tube 81, and a male connector 85 at the other end of the tube 81. The male connector 85 of the enteral giving set 80 will be connected to the patient. By opening the clamp 84, it is possible, using gravity, to allow the liquid substance in the container 1 to pass through the port 50 and the enteral giving set 80 in order, and then to be administered to the patient.

When the container 1 is hung with the port 50 at the bottom as shown in FIG. 4, creases 30*a* and 30*b* passing through the lower sealed protruding portions 20*a* and 20*b* are formed in the sheets 12*a* and 12*b* constituting the container body 10. As the liquid substance flows out from the container 1 as a result of opening the clamp 84, the liquid level 70 of the liquid substance falls and the spacing between the sheets 12*a* and 12*b* gradually decreases in the effective area 14. In this process as well, since the liquid substance accumulates in the lower part of the effective area 14, the spacing between the sheets 12*a* and 12*b* is larger in the lower part of the effective area 14 than in the upper part thereof. Accordingly, as the liquid substance flows out, the creases 30*a* and 30*b* passing through the lower sealed protruding portions 20*a* and 20*b* disappear. The depth of the creases 30*a* and 30*b* (the bending angle of the sheets 12*a* and 12*b*) decreases with a decrease in the amount of the liquid substance remaining in the container 1, but the creases 30*a* and 30*b* always pass through the sealed protruding portions 20*a* and 20*b*.

As has been described thus far, with the container 1 of this embodiment, the creases 31*a* and 31*b* passing through the sealed protruding portions 21*a* and 21*b* are formed in the sheets 12*a* and 12*b* when the container 1 is hung as shown in FIG. 3, and the creases 30*a* and 30*b* passing through the sealed protruding portions 20*a* and 20*b* are formed in the sheets 12*a* and 12*b* when the container 1 is hung as shown in FIG. 4. Consequently, the positions of the creases 30*a*, 30*b*, 31*a*, and 31*b* formed in the sheets 12*a* and 12*b* are always constant, regardless of, for example, the individual difference of the container body 10 and the amount and physical properties (e.g., the viscosity and the presence or absence of any contamination by solids) of the liquid substance in the container body 10. Accordingly, if a scale is provided on the sheet 12*a* (or 12*b*), then the amount of the liquid substance in the container body 10 can be accurately known by using the scale in a state in which the container 1 is hung as shown in FIGS. 3 and 4. That is, in a state in which the container 1 is hung as shown in FIG. 3, a desired amount of a liquid substance can be injected accurately into the container body 10. On the other hand, in a state in which the container 1 is hung as shown in FIG. 4, the amount of a liquid substance in the container body 10 can be accurately known before administering the liquid substance to the patient. Additionally, since the depth of the creases 31*a*, 31*b*, 30*a*, and 30*b* changes according to the amount of the liquid substance in the container 1 as described above, it is preferable that the scale is provided on the sheet 12*a* (or 12*b*) while taking the change in depth of the creases 31*a*, 31*b*, 30*a*, and 30*b* into consideration.

There is no particular limitation with respect to the type of the liquid substance injected into the container 1 of the present invention, and it is possible to use any known nutrients, liquid foods, medications, and infusions used for enthral nutrition, parenteral nutrition, and the like. Examples of oligomeric formulas include "Twinline" (manufactured by: EN Otsuka Pharmaceutical Co., Ltd., sold by: Otsuka Pharmaceutical Co., Ltd.), and examples of polymeric formulas include "Racol" (manufactured by: EN Otsuka Pharmaceutical Co., Ltd., sold by: Otsuka Pharmaceutical Co., Ltd.), "Harmonic-M" (manufactured by: Nutrichem, sold by: SSP CO., LTD/Ajinomoto Pharma Co., Ltd.), "Harmonic-F" (manufactured by: Nutrichem, sold by: SSP CO., LTD/Ajinomoto Pharma Co., Ltd.), and "Ensure Liquid" (manufactured by: Meiji Dairies Corporation, sold by: Dainippon Sumitomo Pharma Co., Ltd./ABBOTT JAPAN CO., LTD.).

The above-described embodiment is merely an example, and the present invention can be changed as appropriate without being limited to this embodiment.

For example, the number, position, shape, size, and the like of the sealed protruding portion are not limited to those in the above-described embodiment, and can be changed as appropriate. The number of sealed protruding portions formed in a single long-side sealed area is not limited to two as in the above embodiment, and may be one or three or more. Although the sealed protruding portion is formed in both of the pair of long-side sealed areas 11La and 11Lb in the above-described embodiment, the sealed protruding portion may be formed in only one of the pair of long-side sealed areas. When the sealed protruding portion is formed in both of the pair of long-side sealed areas as in the above-described embodiment, the position, in the Y-axis direction, of the sealed protruding portion formed in one of the long-side sealed areas may be different from that of the sealed protruding portion formed in the other long-side sealed area. The position of the sealed protruding portion in the Y-axis direction is not limited to those in the above-described embodiment. The shape of the end edge of the sealed protruding portion need not be a substantially semicircular shape as in the above-described embodiment, and may be any shape such as a substantially semi-ellipsoidal shape, a substantially triangular shape, and a substantially quadrangular shape. The size of the sealed protruding portion (e.g., the protruding dimension in the X-axis direction from the long-side sealed area, or the dimension in the Y-axis direction) can be set appropriately taking into consideration the size of the container body, the mechanical property values of the sheets, the formation state of a crease when a liquid substance is injected into the container body, and the like.

The end edge shape, the position, number, and the like of the openings (through-holes) formed in the sealed area 11 of the container body 10 can be changed as appropriate. Alternatively, openings need not be formed in the sealed area 11. Further, the container body need not have the linear fastener 13.

The shape of the port 50 may be appropriately changed according to the use and the like. For example, the inner surface shape of the liquid passage hole 51 formed in the tubular portion 52 need not be a cylindrical surface as in the above-described embodiment, and may be, for example, a polygonal prismatic surface (e.g., a quadrangular prismatic surface or a hexagonal prismatic surface). The holding portion 58 may be omitted. A protrusion, a recess, or the like may be formed in the outer circumferential surface of the tubular portion 52, in order, for example, to facilitate catching of the port 50 with a jig. Also, the shape of the sealing portion 55 is not limited to those shown in the above-described embodiment; for example, the sealing portion 55 may have a columnar shape whose bottom surface is substantially ellipsoidal. A port may be attached to both of the pair of short-side sealed areas 11Sa and 11Sb of the container body.

Although the tube 81 of the enteral giving set 80 is connected to the port 50 serving as a liquid passage portion for providing communication between the interior and the exterior of the container body 10 in the above-described embodiment, the present invention is not limited thereto. For example, the tube of the enteral giving set may be attached to the sealed area 11 of the container body 10 in the same manner as with the port 50 described above.

The configuration of the enteral giving set used for the container 1 is not limited to that shown in FIG. 4, and any well-known tube used for enthral nutrition, parenteral nutrition, and the like may be selected as appropriate.

The above-described embodiment is intended merely to clarify the technical content of the present invention. The present invention is not to be construed as limited to these specific examples, but to be construed in a broad sense, and may be practiced with various modifications within the sprit of the invention and the scope of the claims.

INDUSTRIAL APPLICABILITY

Although there is no particular limitation with respect to the field to which the present invention is applied, the invention can be preferably used as a medical container and a medical container set used for providing enteral nutrition, parenteral nutrition, and the like.

The invention claimed is:

1. A medical container comprising a bag-like container body made up of two flexible sheets, wherein the container body has a pair of long-side sealed areas formed by the two sheets being bonded together along two opposing sides that are substantially parallel to a major axis direction of the container body, at least one of the two sheets is provided with a scale for indicating an amount of a liquid substance in the container body in a state in which the medical container is hung in the major axis direction with an end of the container body at top, at least one of the pair of long-side sealed areas is provided with a first sealed protruding portion protruding toward the other long-side sealed area such that the spacing between the pair of long-side sealed areas is locally narrowed, the first sealed protruding portion is positioned on a first side in the major axis direction relative to a central position of an effective area of the container body capable of storing the liquid substance, at least one of the pair of long side sealed area is provided with a second sealed protruding portion protruding toward the other long-side sealed area such that the spacing between the pair of long-side sealed areas is locally narrowed, the second sealed protruding portion is positioned on a second side in the major axis direction relative to the central position of the effective area, and a crease passing through a lower one of the sealed protruding portions is formed in the sheets when the liquid substance has been injected into the container body in a volume greater than or equal to 10% of a defined volume of the container body and the medical container is hung such that the major axis direction is parallel to the direction of gravity.

2. The medical container according to claim 1, wherein the first sealed protruding portion is formed in both of the pair of long-side sealed areas, and the second sealed protruding portion is formed in both of the pair of long-side sealed areas.

3. The medical container according to claim 2, wherein the positions of the first sealed protruding portions formed in both of the pair of long-side sealed areas coincide with each other in the major axis direction, and the positions of the second sealed protruding portions formed in both of the pair of long-side sealed areas coincide with each other in the major axis direction.

4. The medical container according to claim 1, wherein each sealed protruding portion has a substantially semicircular shape.

5. The medical container according to claim 1, wherein each sealed protruding portion is located at a distance of ¼ to ½, inclusive, of the spacing between the pair of long-side sealed areas in the major axis direction from one end, in the major axis direction, of the effective area of the container body.

6. A medical container set comprising the medical container according to claim 1, and an enteral giving set including a flexible tube for removing a liquid substance stored in the container body.

* * * * *